United States Patent
Bristow

(10) Patent No.: US 10,568,329 B2
(45) Date of Patent: Feb. 25, 2020

(54) SYNERGISTIC INSECTICIDAL COMPOSITION

(71) Applicant: ROTAM AGROCHEM INTERNATIONAL COMPANY LIMITED, Chai Wan (HK)

(72) Inventor: James Timothy Bristow, Chai Wan (HK)

(73) Assignee: ROTAM AGROCHEM INTERNATIONAL COMPANY LIMITED, Chai Wan (HK)

(*) Notice: Subject to any disclaimer, the term of this patent is extended or adjusted under 35 U.S.C. 154(b) by 0 days.

(21) Appl. No.: 15/552,743

(22) PCT Filed: Mar. 4, 2016

(86) PCT No.: PCT/CN2016/075567
§ 371 (c)(1),
(2) Date: Aug. 22, 2017

(87) PCT Pub. No.: WO2016/155462
PCT Pub. Date: Oct. 6, 2016

(65) Prior Publication Data
US 2018/0049439 A1    Feb. 22, 2018

(30) Foreign Application Priority Data

Mar. 31, 2015    (GB) .................. 1505594.0

(51) Int. Cl.
*A01N 47/24*    (2006.01)
*A01N 53/00*    (2006.01)
*A61K 31/222*    (2006.01)
*A61K 31/325*    (2006.01)

(52) U.S. Cl.
CPC ............ *A01N 47/24* (2013.01); *A01N 53/00* (2013.01); *A61K 31/222* (2013.01); *A61K 31/325* (2013.01); *A01N 2300/00* (2013.01)

(58) Field of Classification Search
None
See application file for complete search history.

(56) References Cited

FOREIGN PATENT DOCUMENTS

| | | |
|---|---|---|
| CN | 1107651 A | 9/1995 |
| CN | 1142744 A | 2/1997 |
| CN | 1148934 A | 5/1997 |
| CN | 1206554 A1 | 2/1999 |
| CN | 1270766 A | 10/2000 |
| CN | 103053600 A | 4/2013 |
| CN | 103371168 A | 10/2013 |
| CN | 103651546 A | 3/2014 |
| CN | 104286041 A | 1/2015 |
| CN | 104322547 A | 2/2015 |
| WO | 2012165126 A1 | 12/2012 |

OTHER PUBLICATIONS

All, J. N. et al., Florida Entomologist (1986), 69(3), pp. 598-602).*
Castle et al., California Agriculture (1996), 50(1):18-23, pp. 1/11-11/11.*
Bielza et al., Pest Management Science (2007), 63(1), pp. 84-89.*
International Search Report for PCT/CN2016/075567 dated Jun. 3, 2016.
Combined Search and Examination Report for Application No. GB1505594.0.
Tsai, Y.S. etc. "Effect of insecticides on the virulence of the green muscardine fungus, *Metarhizium anisopliae* var. *anisopliae*, against the beet armyworm, *Spodoptera exigua*" (Zhiwu Baohu Xuehui Huikan), vol. 34, No. 3, Dec. 31, 1992 (Dec. 31, 1992), pp. 216-226.

* cited by examiner

*Primary Examiner* — Brian J Davis
(74) *Attorney, Agent, or Firm* — Dickinson Wright PLLC

(57) ABSTRACT

A synergistic insecticidal composition comprising two components: (A) at least one carbamate insecticide and (B) at least one pyrethroid insecticide is provided. There is also provided a process for preparing the insecticidal composition. A method to prevent, control and/or treat insect infestations in plants, plant parts and/or their surroundings by applying the synergistic insecticidal composition comprising the two components (A) and (B) is also provided.

12 Claims, No Drawings

SYNERGISTIC INSECTICIDAL COMPOSITION

This application is a 371 national phase entry of PCT/CN2016/075567 filed 4 Mar. 2016, which claims benefit of GB Application No. 1505594.0, filed 31 Mar. 2015, the entire contents of which are incorporated herein by reference for all purposes.

BACKGROUND

1. Field

The present invention relates to a synergistic insecticidal composition comprising two active components. The present invention also relates to a process for preparing the insecticidal composition. The present invention also relates to a method to prevent, control and/or treat insect infestations in plants, plant parts and/or their surroundings by applying the synergistic insecticidal composition.

2. Related Art

Insect infestations represent a major threat to economically important agricultural crops. The yield of plants, for example, cereals, citrus, cucurbitaceae, fibre plants, fruits, leguminous plants, ornamentals and vegetables, are adversely impacted by insect attack.

Chemical control is an important way for preventing and controlling pests in agriculture. However, current agents show unsatisfactory effects to certain kinds of pests. Furthermore, many pests have developed resistance to commonly used pesticides due to a long term use of the pesticides. Therefore, there is an urgent need to develop new methods and pesticides to control these pests. Moreover, the environmental and economic requirements imposed on modern-day insecticides are continually increasing, with regard, for example, to the spectrum of action, toxicity, selectivity, application rate, formation of residues, and favorable preparation ability. Since there may be problems, for example, with resistances developing to known active compounds, a constant task is to develop new insecticide agents which in some areas at least have advantages over their known counterparts.

Carbamates are a known class of insecticidally active compounds. Examples of carbamate insecticides are alanycarb, aldicarb, aldoxycarb, allyxycarb, aminocarb, bendiocarb, benfuracarb, bufencarb, butacarb, butocarboxim, butoxycarboxim, carbanolate, carbaryl, carbofuran, carbosulfan, cloethocarb, CPMC, decarbofuran, dicresyl, dimetan, dimethacarb, dimetilan, dioxacarb, EMPC, ethiofencarb, fenethacarb, fenobucarb, furathiocarb, hyquincarb, isolan, isoprocarb, methiocarb, methomyl, metolcarb, mexacarbate, nitrilacarb, oxamyl, pirimicarb, promacyl, promecarb, propoxur, pyramat, pyrolan, tazimcarb, thiocarboxime, thiodicarb, thiofanox, trimethacarb, XMC and xylylcarb.

However, experience with the single active straight formulation of insecticides worldwide indicates there is a high risk of development of resistant insect subpopulations. Resistance has been reported worldwide in an increasing number of insects active in field crops, fruit, vegetables, and so on.

Pyrethroids are known insecticides and are synthesized derivatives of naturally occurring pyrethrins, which are taken from pyrethrum, the oleoresin extract of dried chrysanthemum flowers. Ketoalcoholic esters of chrystanthemic and pyrethroic acid account for the insecticidal properties of pyrethrins. These acids are lipophilic and penetrate insects and paralyze their nervous system (Reigart, et al., 1999). The insecticidal action of pyrethroid is widely known to be effective against a variety of insect pests in many major crops such as fruits, vegetables, cereals, maize, cotton, soybean, grapes and even on public and animal health sectors. The activity of pyrethroids is both contact and stomach action as a broad spectrum insecticides. Examples of synthetic pyrethroids are deltamethrin, lambda-cyhalothrin, fenvalerate, permethrin, cypermethrin, bifenthrin, esfenvalerate, etofenprox, cyfluthrin, fenpropathrin, allethrin, cyphenothrin, flucythrinate, flumethrin, imiprothrin, metofluthrin, prallethrin, resmethrin, silafluofen, sumithrin, tefluthrin, tetramethrin, tralomethrin and transluthrin.

Enhancements of insecticidal agents and compositions have been achieved to improve control of insect pests and application practice to target crops as single or mixed pesticides. The judicious use of adopting strip application or spot application on areas with high insect incidence only and soil application to avoid direct contact with natural enemies and the use of selective and non-persistent agents increase environmental safety and lower incidence of insect resistance. In addition, the adoption of the rotational application of insect control agents with different modes of action contributes to good pest management. Having an insecticidal composition with a high synergistic action with no cross resistance to existing insecticide agents and with a low environmental impact is desirable. Therefore, it would be advantageous to provide a composition, which is potent to insect attack, with physico compatible formulations stable in during storage, safely pack and in ready-to-use formulation.

SUMMARY

The present invention provides a synergistic insecticidal composition comprising as component (A) at least one carbamate insecticide and as component (B) at least one pyrethroid insecticide.

The present invention also provides a method to control insect infestations in plants, plant parts and/or their surroundings by applying a synergistic insecticidal composition comprising the above components (A) and (B) on the plants, plant parts and/or surrounding.

The present invention also provides a process for making a synergistic insecticidal composition containing as component (A) at least one carbamate insecticide and as component (B) at least one pyrethroid insecticide.

The present invention also provides the use of a synergistic insecticidal composition comprising the above components (A) and (B) to prevent, control and/or treat insect infestations in plants, plant parts and/or surrounding.

DETAILED DESCRIPTION OF EXAMPLE EMBODIMENTS

"Plant" as used herein, refers to all plant and plant populations such as desired and undesired wild plants or crop plants.

"Plant parts" as used herein, refers to all parts and organs of plants, such as shoot, leaves, needles, stalks, stems, fruit bodies, fruits, seeds, roots, tubers and rhizomes. Harvested materials, and vegetative and generative propagation materials, for example, cutting, tubers, meristem tissue, rhizomes, offsets, seeds, single and multiple plant cells and any other plant tissues, are also included.

The word "surroundings" refers to the place on which the plants are growing, the place on which the plant propagation materials of the plants are sown or the place on which the plant propagation materials of the plants will be sown.

"At least one" designates a number of the respective compounds of 1, 2, 3, 4, 5, 6, 7, 8, 9 or more, preferably 1, 2, or 3.

It has now surprisingly been found that when applying an insecticidal composition comprising as component (A) at least one carbamate insecticide and as component (B) at least one pyrethroid insecticide on the plants, plant parts and/or their surroundings, for example corn, cotton, dry bean, lemon, melon, orange, papaya, potato, rose, soybean, tomato and wheat, an excellent performance in preventing, controlling and treating insect infestations may be observed. The synergistic insecticidal composition is highly effective for the protection of the aforementioned crops from insect attack.

The synergistic insecticidal composition is found to be highly active against a wide range of pests, i.e., aphids, armyworms, beetles, bollworm, budworms, pickleworm, burrowing bugs, borers, caterpillars, citrus Orthezia, Great Southern White, leafhoppers, leafminers, loopers, millipedes, broad mites, moths, spider mites, stink bugs, thrips, weevils, whiteflies, worms, psylla. The present compositions are particular effective against armyworms, budworms, burrowing bugs, borers, loopers, broad mites, moths, spider mites, stink bugs and worms.

Embodiments also demonstrate reduced application cost, increased crop yield and reduced environmental risk. It also delays the dominance of resistant strains of pests, has a broader spectrum of activity and reduces risk of developing resistance.

Another objective is to provide a process for using the synergistic insecticidal composition containing a carbamate compound and a pyrethroid compound. The advantage of the process relates to the propagation of part of plants and especially the seeds, as coated with and/or containing the synergistic composition of the component (A) at least one carbamate insecticide and (B) at least one pyrethroid insecticide.

The components (A) and (B) may be applied to the plants or plant materials in any desired sequence, any combination, consecutively or simultaneously.

The component (A) carbamate insecticide may be present in the composition in any suitable amount, and is generally present in an amount of from about 1% to about 75% by weight of the composition, preferably from about 5% to about 60%, from about 10% to about 45% by weight of the composition, more preferably from about 15% to about 30% by weight of the composition, even more preferably from about 15% to about 25% by weight, even more preferred more from about 17% to about 23% by weight, most preferably about 20%.

The component (A) carbamate insecticides may be any insecticidally active carbamate compounds, for example with such compounds being known in the art and commercially available. The component (A) is preferably one or more selected from alanycarb, aldicarb, aldoxycarb, allyxycarb, aminocarb, bendiocarb, benfuracarb, bufencarb, butacarb, butocarboxim, butoxycarboxim, carbanolate, carbaryl, carbofuran, carbosulfan, cloethocarb, CPMC, decarbofuran, dicresyl, dimetan, dimethacarb, dimetilan, dioxacarb, EMPC, ethiofencarb, fenethacarb, fenobucarb, furathiocarb, hyquincarb, isolan, isoprocarb, methiocarb, methomyl, metolcarb, mexacarbate, nitrilacarb, oxamyl, pirimicarb, promacyl, promecarb, propoxur, pyramat, pyrolan, tazimcarb, thiocarboxime, thiodicarb, thiofanox, trimethacarb, XMC and xylylcarb.

Preferably, the component (A) is selected from methiocarb, methomyl, oxamyl, pirimicarb and thiodicarb. Most preferably, the component (A) is methomyl.

The component (B) pyrethroid insecticide may be present in the composition in any suitable amount, and is generally present in an amount of from about 1% to about 50% by weight of the composition, preferably from about 1% to about 40%, from about 1% to about 30%, from about 1% to about 20% by weight of the composition, more preferably from about 1% to about 10% by weight of the composition, even more preferred from about 1% to about 8% by weight of the composition, even more preferably from about 1% to about 5% by weight of the composition, or from about 2% to 3% by weight of the composition, and most preferably 2.5%.

The component (B) pyrethroid insecticide may be any insecticidally active pyrethroid compound, for example with such compounds being known in the art and available commercially. The pyrethroid compound is preferably one or more selected from deltamethrin, lambda-cyhalothrin, fenvalerate, permethrin, cypermethrin, bifenthrin, esfenvalerate, etofenprox, cyfluthrin, fenpropathrin, allethrin, cyphenothrin, flucythrinate, flumethrin, imiprothrin, metofluthrin, prallethrin, resmethrin, silafluofen, sumithrin, tefluthrin, tetramethrin, tralomethrin and transluthrin.

Preferably, the compound (B) is selected from deltamethrin, lambda-cyhalothrin, cypermethrin, bifenthrin, esfenvalerate, etofenprox, tefluthrin, preferably selected from cypermethrin, bifenthrin, esfenvalerate, etofenprox and tefluthrin. Most preferably, the component (B) is bifenthrin.

The components (A) and (B) may be present in the composition or applied in any amounts relative to each other, to provide the synergistic effect of the mixture. In particular, the weight ratio of the components (A) and (B) in the composition independently is preferably in the range of from about 99:1 to about 99:1, about 50:1 to about 1:50, about 25:1 to about 1:25, about 20:1 to about 1:20, more preferably from about 15:1 to about 1:15 or about 12:1 to about 1:12. Preferably, the weight ratio of the components (A) to (B) in the composition is about 8:1.

The components (A) and (B) together may be present in the composition in any suitable amount, and are generally present in a total amount of from about 5% to about 90% by weight of the composition, preferably from about 15% to about 50% by weight of the composition more preferably from about 20% to about 30% by weight of the composition.

Preferably each combination is a composition comprising, components (A) and (B), and optionally one or more auxiliaries. The auxiliaries employed in the composition will depend upon the type of formulation and/or the manner in which the formulation is to be applied by the end user. Formulations incorporating the composition are described hereinafter. Suitable auxiliaries which may be comprised in the composition are all customary formulation adjuvants or components, such as extenders, carriers, solvents, surfactants, stabilizers, anti-foaming agents, anti-freezing agents, preservatives, antioxidants, colorants, thickeners, solid adherents and inert fillers. Such auxiliaries are known in the art and are commercially available. Their use in the formulation of the compositions will be apparent to the person skilled in the art.

The composition may further comprise one or more inert fillers. Such inert fillers are known in the art and available commercially. Suitable fillers in a form of a solid include, for example, natural ground minerals, such as kaolins, aluminas, talc, chalk, quartz, attapulgite, montmorillonite, and diatomaceous earth, or synthetic ground minerals, such as highly dispersed silicic acid, aluminum oxide, silicates, and calcium phosphates and calcium hydrogen phosphates. Suitable inert fillers for granules include, for example, crushed and fractionated natural minerals, such as calcite, marble, pumice, sepiolite, and dolomite, or synthetic granules of inorganic and organic ground materials, as well as granules of organic material, such as sawdust, coconut husks, corn cobs, and tobacco stalks.

The composition optionally includes one or more surfactants which are preferably non-ionic, cationic and/or anionic in nature and surfactant mixtures which have good emulsifying, dispersing and wetting properties, depending on the nature of the active compound to be formulated. Suitable surfactants are known in the art and are commercially available. Suitable anionic surfactants can be both so-called water-soluble soaps and water-soluble synthetic surface-active compounds. Soaps which may be used are the alkali metal, alkaline earth metal or substituted or unsubstituted ammonium salts of higher fatty acid ($C_{10}$-$C_{22}$), for example the sodium or potassium salt of oleic or stearic acid, or of natural fatty acid mixtures. The surfactant can be an emulsifier, dispersant or wetting agent of ionic or nonionic type. Examples which may be used are salts of polyacrylic acids, salts of lignosulphonic acid, salts of phenylsulphonic or naphthalenesulphonic acids, polycondensates of ethylene oxide with fatty alcohols or with fatty acids or with fatty amines, substituted phenols, especially alkylphenols, sulphosuccinic ester salts, taurine derivatives, especially alkyltaurates, or phosphoric esters of polyethoxylated phenols or alcohols. The presence of at least one surfactant is generally required when the active compound and/or the inert carrier and/or auxiliary/adjuvant are insoluble in water and the vehicle for the final application of the composition is water.

The composition optionally further comprises one or more polymeric stabilizers. The suitable polymeric stabilizers that may be used include, but are not limited to, polypropylene, polyisobutylene, polyisoprene, copolymers of monoolefins and diolefins, polyacrylates, polystyrene, polyvinyl acetate, polyurethanes or polyamides. Suitable stabilizers are known in the art and commercially available.

The surfactants and polymeric stabilizers mentioned above are generally believed to impart stability to the composition, in turn allowing the composition to be formulated, stored, transported and applied.

Suitable anti-foams include all substances which can normally be used for this purpose in agrochemical compositions. Suitable anti-foam agents are known in the art and are available commercially. Particularly preferred antifoam agents are mixtures of polydimethylsiloxanes and perfluroalkylphosphonic acids, such as the silicone anti-foam agents available from GE or Compton.

Suitable organic solvents are selected from all customary organic solvents which thoroughly dissolve the active compounds employed. Again, suitable organic solvents for the active components (A) and (B) are known in the art. The following may be mentioned as being preferred: N-methyl pyrrolidone, N-octyl pyrrolidone, cyclohexyl-1-pyrrolidone; or SOLVESSO™200, a mixture of paraffinic, isoparaffinic, cycloparaffinic and aromatic hydrocarbons. Suitable solvents are commercially available.

Suitable preservatives include all substances which can normally be used for this purpose in agrochemical compositions of this type and again are well known in the art. Suitable examples that may be mentioned include PREVENTOL® (from Bayer AG) and PROXEL® (from Bayer AG).

Suitable antioxidants are all substances which can normally be used for this purpose in agrochemical compositions, as is known in the art. Preference is given to butylated hydroxytoluene.

Suitable thickeners include all substances which can normally be used for this purpose in agrochemical compositions. For example xanthan gum, PVOH, cellulose and its derivatives, clay hydrated silicates, magnesium aluminum silicates or a mixture thereof. Again, such thickeners are known in the art and are available commercially.

The composition may further comprise one or more solid adherents. Such adherents are known in the art and available commercially. They include organic adhesives, including tackifiers, such as celluloses of substituted celluloses, natural and synthetic polymers in the form of powders, granules, or lattices, and inorganic adhesives such as gypsum, silica or cement.

In addition, depending upon the formulation, the composition may also comprise water.

According to a preferred embodiment, the insecticidal composition comprises as component (A) methomyl and as component (B) bifenthrin.

The compositions can be used in the agricultural sector and related fields of use for prevent and control insects example, but not limited to:

Maecolaspis trivialis, Faustinus cubae, aphid (Aphis gossypii, Brevicoryne brassicae, Macrosiphum euphorbiae, Myzus persicae, Macrosiphum euphorbiae, Rhopalosiphum graminum), armyworm (Pseudaletia sequax, Pseudaletia adultera), Bean leafhopper (Empoasca kraemeri), bean shoot moth (Epinotia aporema), Beetle (Diabrotica speciosa, Migdolus fryanus, Diloboderus abderus, Rhyzopertha dominica), black cutworm (Agrotis ipsilon), boll weevil (Anthonomus grandis), bollworm (Helicoverpa armigera), borer (Ecdytolopha aurantiana, Neoleucinodes elegantalis), broad mite (Polyphagotarsonemus latus), burrowing bug (Scaptocoris castanea), caterpillar (Pseudoplusia includens), citrus orthezia (Orthezia praelonga), citrus red mite (Panonychus citri), corn earworm (Helicoverpa zea), cotton leafworm (Alabama argillacea), diamondback moth (Plutella xylostella), fall armyworm (Spodoptera frugiperda), false spider mite (Brevipalpus phoenicis), great Southern White (Ascia monuste orseis), great Southern White (Ascia monuste orseis), leafhopper (Empoasca kraemeri), leafhoppers (Oncometopia facialis), leafminer (Lyriomyza huidobrensis), looper (Pseudoplusia includens, Rachiplusia nu, Chrysodeixis includens), melonworm moth (Diaphania hyalinata), millipedes (Juls hesperus, Julus sp.), pea leafminer (Lyriomyza huidobrensis), pickleworm (Diaphania nitidalis), potato tuber moth (Phthorimaea operculella), red spidermite (Panonychus ulmi), spider mite (Mononychellus planki), stink bug (Nezara viridula, Euschistus heros Piezodorus guildinii, Dichelops melancanthus, termite (Procornitermes triacifer, Heterotermes tenuis), thrips (Caliothrips bicinctus, Caliothrips brasiliensis, Frankliniella schultzei, Selenothrips rubrocinctus), tobacco budworm (Heliothis virescens), tobacco flea beetle (Epitrix fasciata), tomato fruit borer (Neoleucinodes elegantalis), tomato leafminer (Tuta absolute), two-spotted spider mite (Tetranychus urticae), velvetbean caterpillar Moth (Anticarsia gemmatalis), weevil (Acanthoscelides obtectus, Sitophilus zeamais), whitefly (Bemisia tabaci).

The compositions exhibit surprisingly high effectiveness in controlling insect infestations caused by:

two spotted spidermite (Tetranychus urticae Koch), red spidermite (Panonychus ulmi), broad mite (Polyphagotarsonemus latus) on citrus, like orange, lemon;

budworm (*Heliothis virescens*), burrowing bug (*Scaptocoris castanea*), two spotted spidermite (*Tetranychus urticae* Koch), red spidermite (*Panonychus ulmi*), broad mite (*Polyphagotarsonemus latus*) on cotton;

bollworm (*Helicoverpa armigera*) on dry bean;

melonworm moth (*Diaphania hyalinata*) and pickleworm (*Diaphania nitidalis*) on melon;

stink bugs (*Euschistus heros, Nezara viridula, Piezodorus guildinii, Dichelops melancanthus*), spidermite (*Mononychellus planki*), two spotted spidermite (*Tetranychus urticae*), loopers (*Chrysodeixis* includes), fall armyworm (*Spodoptera frugiperda*), bollworm (*Helicoverpa armigera*) on soybean;

potato tuber moth (*Phthorimaea operculella*) on potato; and fruit borer (*neoleucinodes elegantalis*) on tomato.

The compositions are suitable for plants of the crops: cereals (wheat, barley, rye, oats, corn, rice, sorghum, triticale and related crops); fruit, such as pomes, stone fruit and soft fruit, such as apples, grapes, pears, plums, peaches, papayas, almonds, pistachio, cherries, and berries, for example strawberries, raspberries and blackberries, bell pepper, red pepper; leguminous plants (beans, lentils, peas, soybeans, dry beans); oil plants (rape, mustard, sunflowers); cucurbitaceae (marrows, cucumbers, melons); fibre plants (cotton, flax, hemp, jute); citrus, such as calamondin, citrus citron, citrus hybrids (includes chironja, tangelo, tangor), grapefruit, kumquat, lemon, lime, mandarin (tangerine), sour orange, sweet orange, pummelo, and satsuma mandarin; vegetables (spinach, lettuce, asparagus, cabbages, carrots, onions, tomatoes, potatoes, paprika); coffee; as well as ornamentals (flowers, such as rose, shrubs, broad-leaved trees and evergreens, such as conifers).

The compositions may be applied on cereals, citrus, cucurbitaceae, fibre plants, fruits, leguminous plants, ornamentals and vegetables. Also, the compositions may be applied on corn, cotton, dry bean, lemon, melon, orange, papaya, potato, rose, soybean, tomato and wheat.

In one embodiment, compositions are particularly effective in controlling:

two spotted spidermite (*Tetranychus urticae* Koch), red spidermite (*Panonychus ulmi*), broad mite (*Polyphagotarsonemus latus*) on citrus, like orange, lemon;

budworm (*Heliothis virescens*), burrowing bug (*Scaptocoris castanea*), two spotted spidermite (*Tetranychus urticae* Koch), red spidermite (*Panonychus ulmi*), broad mite (*Polyphagotarsonemus latus*) on cotton;

bollworm (*Helicoverpa armigera*) on dry bean;

melonworm moth (*Diaphania hyalinata*) and pickleworm (*Diaphania nitidalis*) on melon;

stink bugs (*Euschistus heros, Nezara viridula, Piezodorus guildinii, Dichelops melancanthus*), spidermite (*Mononychellus planki*), two spotted spidermite (*Tetranychus urticae*), loopers (*Chrysodeixis* includes), fall armyworm (*Spodoptera frugiperda*), bollworm (*Helicoverpa armigera*) on soybean;

potato tuber moth (*Phthorimaea operculella*) on potato; and fruit borer (*neoleucinodes elegantalis*) on tomato;

the plants, their plant parts and/or surroundings being treated by applying a synergistic insecticidal composition comprising (A) methomyl and (B) bifenthrin, wherein the weight ratio of the components (A) to (B) in the composition is about 8:1.

In a further embodiment, the composition is particularly effective in controlling:

two spotted spidermite (*Tetranychus urticae* Koch), red spidermite (*Panonychus ulmi*), broad mite (*Polyphagotarsonemus latus*) on citrus, like orange, lemon;

budworm (*Heliothis virescens*), burrowing bug (*Scaptocoris castanea*), two spotted spidermite (*Tetranychus urticae* Koch), red spidermite (*Panonychus ulmi*), broad mite (*Polyphagotarsonemus latus*) on cotton;

bollworm (*Helicoverpa armigera*) on dry bean;

melonworm moth (*Diaphania hyalinata*) and pickleworm (*Diaphania nitidalis*) on melon;

stink bugs (*Euschistus heros, Nezara viridula, Piezodorus guildinii, Dichelops melancanthus*), spidermite (*Mononychellus planki*), two spotted spidermite (*Tetranychus urticae*), loopers (*Chrysodeixis* includes), fall armyworm (*Spodoptera frugiperda*), bollworm (*Helicoverpa armigera*) on soybean;

potato tuber moth (*Phthorimaea operculella*) on potato; and fruit borer (*neoleucinodes elegantalis*) on tomato, by applying to their plant parts and/or surrounding a synergistic insecticidal composition comprising components (A) methomyl and (B) bifenthrin, wherein the weight of the component (A) is about 20% by weight of the composition and; wherein the component (B) is about 2.5% by weight of the composition.

The compositions can be applied to the foliage or fruit of the plant or their surroundings.

The use of an insecticidal composition as described herein for preventing, controlling and/or treating insect infestations in plants, plant parts and/or their surroundings is also described.

The composition may contain or be mixed with other pesticides, such as fungicides, other insecticides and nematicides, growth factor enhancers and fertilizers.

The rates of application (use) of the composition may vary, for example, according to type of use, type of crop, the specific active compounds in the combination, type of plants, but is such that the active compounds in the combination are applied in an effective amount to provide the desired action (such as insects or pest control). The application rate of the composition for a given set of conditions can readily be determined by trials.

The components (A) and (B), and any other pesticides, may be applied and used in pure form, as a solid active compound, for example, in a specific particle size, or preferably together with at least one of the auxiliary or adjuvant components, as is customary in formulation technology, such as extenders, for example solvents or solid carriers, or surface-active compounds (surfactants), as described in more detail above. Generally, the components (A) and (B) are in the form of a formulation composition with one or more of the aforementioned customary formulation auxiliaries.

Examples of formulation types for pre-mix compositions are:

a water-soluble concentrate (SL), an emulstifiable concentrate (EC), an emulsion (EW), a micro-emulsion (ME), an oil-based suspension concentrate (OD), a flowable suspension (FS), a water-dispersible granule (WG), a water-soluble granule (SG), a water-dispersible powder (WP), a water soluble powder (SP), a granule (GR), an encapsulated granule (CG), a fine granule (FG), a macrogranule (GG), an aqueous suspo-emulsion (SE), a microencapsulated suspension (CS), a microgranule (MG) or preferably a suspension concentrate (SC) and an emulsifiable concentrate (EC).

Using such formulations, either straight (that is undiluted) or diluted with a suitable solvent, especially water, plants, plant parts and/or their surroundings can be treated and protected against insects by spraying, pouring or immersing. Generally, a formulation can be diluted with water having the rate of 1-1000 mL or 10-800 mL or 20-600 mL or 50 mL or 100 mL of composition in 100 L of water. Formulations can be also diluted with water having the rate of from about 1 to about 1000 g total active ingredients per hectare, preferably from about 10 to about 800 g total active ingredients per hectare. Preferably, from about 1-800 g/ha of the component (A) and from about 0.5-2000 g/ha of the component (B), more preferably, from about 10-600 g/ha of the component (A) and from about 1-150 g/ha of the component (B), still more preferably from about 50-400 g/ha of the component (A) and from about 5-100 g/ha of the component (B), still more preferably from about 100-300 g/ha of the component (A) and from about 5-50 g/ha of the component (B), most preferably, from about 150-300 g/ha of the component (A) and 20-40 g/ha of the component (B).

The compositions or components (A) and (B) can be applied using any methods known in the art. These methods include coating, spraying, dipping, soaking, injection, irrigation, etc.

The active components (A) and (B) can be applied to the plants, plant parts and/or their surroundings where control is desired either simultaneously or in succession at short intervals, for example on the same day. The components (A) and (B) may be applied to the plant, one or more parts thereof (such as leaves or seeds), or their surroundings in any order. Each component may be applied just once or a plurality of times. Preferably, each of the components (A) and (B) is applied a plurality of times, in particular from 2 to 5 times, more preferably 1-3 times per season.

The active components (A) and (B) may be applied in any suitable form, as described above. Typically, the active components will be applied as formulations, that is compositions comprising one or more of the active components together with further carriers, surfactants or other application-promoting adjuvants customarily employed in formulation technology.

In the event components (A) and (B) are applied simultaneously, they may be applied as a composition containing components (A) and (B), in which case components (A) and (B) can be obtained from a separate formulation source and mixed together (known as a tank-mix, ready-to-apply, spray broth, or slurry), optionally with other pesticides, or components (A) and (B) can be obtained as a single formulation mixture source (known as a pre-mix, concentrate, formulated compound (or product)), and optionally mixed together with other pesticides.

The compositions are especially well tolerated by plants and are environmentally friendly.

Each composition is especially advantageous for the treatment of plants.

The following examples are given by way of illustration and not by way of limitation of the invention.

Formulation Examples

Water-dispersible granules (WG) were prepared by mixing finely ground active ingredients with auxiliaries (0.5% SUPRALATE® (sodium lauryl sulfate, Witco Inc., Greenwich), 5% REAX®88B (sodium lignosulfonate, Westvaco Corp), Potassium carbonate (balance to 100%)) and then extruded and dried in an airflow drier.

For example,

| | |
|---|---|
| Methomyl | 40% |
| Bifenthrin | 5% |
| SUPRALATE ® (sodium lauryl sulfate, Witco Inc., Greenwich) | 0.5% |
| REAX ®88B (sodium lignosulfonate, Westvaco Corp) | 5% |
| Potassium carbonate | 72% |

Aqueous suspension concentrates (SC) were prepared by mixing finely ground active ingredients with auxiliaries (10% Propylene glycol, 5% Tristyrylphenol ethoxylates, 1% Sodium lignosulfonate, 1% Carboxymethylcellulose, 1% Silicone oil (in the form of a 75% emulsion in water), 0.1% Xanthan gum, 0.1% NIPACIDE BIT 20, Water (Balance to 1 L).

For example,

| | |
|---|---|
| Methomyl | 20% |
| Bifenthrin | 2.5% |
| Propylene glycol | 10% |
| Tristyrylphenol ethoxylates | 5% |
| Sodium lignosulfonate | 1% |
| Carboxymethylcellulose | 1% |
| Silicone oil (in the form of a 75% emulsion in water) | 1% |
| Xanthan gum | 0.1% |
| NIPACIDE BIT 20 | 0.1% |
| Water | Balance to 1 L |

Emulsifiable concentrates (EC) were prepared by mixing active ingredients with auxiliaries (50 g Tristyrylphenol ethoxylates, 1 g Silicone oil, 300 g N-methylpyrrolidone, SOLVESSO 200 (Balance to 1 L).

For example,

| | |
|---|---|
| Methomyl | 200 g |
| Bifenthrin | 25 g |
| Abamectin | 7.2 g |
| Tristyrylphenol ethoxylates | 50 g |
| Silicone oil | 1 g |
| N-methylpyrrolidone | 300 g |
| SOLVESSO 200 | Balance to 1 L |

Biological Examples

A synergistic effect exists with a combination of two active compounds when the activity of a composition comprising both active compounds is greater than the sum of the activities of the two active compounds applied individually. The expected activity for a given combination of two active compounds can be calculated by the so called "Colby equation" (see S. R. Colby, "Calculating Synergistic and Antagonistic Responses of Herbicide Combinations", Weeds 1967, 15, 20-22):

whereby:

A=the activity percentage of compound A when active compound A is empolyed at an application rate of m g/ha;

B=the activity percentage of compound B when active compound B is empolyed at an application rate of n g/ha;

E=the percentage of estimated activity when compounds A and B are empolyed together at an application rate of m g/ha and n g/ha;

then:

$$E=A+B-(A \times B/100).$$

If the actual activity observed for the combination of compounds A and B is greater than that calculated, then the activity of the combination is superadditive. In other words, synergism is present.

Field Test 1—Orange—Spider Mites (*Tetranychus urticae*)

Spider mites (*Tetranychus urticae*) were reared in the laboratory. The number of mites were counted, collected and then put on healthy young orange plants. 75 mL of the formulations were diluted in 100 L of water and then sprayed on the plants until ran off. After staying in a greenhouse at 21-25° C. and 80% relative atmospheric humidity for 10 days, the remaining population of mites was examined. (Table A)

TABLE A

| Test | Formulation | Methomyl (%) | Bifenthrin (%) | Spider mites population (%) |
|---|---|---|---|---|
| Untreated | — | 0 | 0 | 85 |
| 1 | EC | 50 | 0 | 45 |
| 2 | SC | 0 | 40 | 70 |
| 3 | EC | 5 | 20 | 15 |
| 4 | SC | 5 | 40 | 10 |
| 5 | EC | 10 | 30 | 10 |
| 6 | EC | 20 | 2.5 | 0 |
| 7 | SC | 20 | 2.5 | 5 |
| 8 | EC | 30 | 1 | 15 |
| 9 | WG | 40 | 10 | 10 |
| 10 | WG | 50 | 5 | 5 |

Field Test 2—Orange—Red Spidermite (*Panonychus ulmi*)

Red spidermite (*Panonychus ulmi*) were reared in the laboratory. The number of mites were counted, collected and then put on healthy young orange plants. 50 mL of formulations were diluted in 100 L of water and then sprayed on the plants until ran off. After staying in a greenhouse at 21-25° C. and 80% relative atmospheric humidity for 10 days, the remaining population of mites was examined. (Table B)

TABLE B

| Test | Formulation | Methomyl (%) | Bifenthrin (%) | Spider mites population (%) |
|---|---|---|---|---|
| Untreated | — | 0 | 0 | 80 |
| 1 | EC | 50 | 0 | 45 |
| 2 | SC | 0 | 40 | 65 |
| 3 | EC | 5 | 20 | 15 |
| 4 | SC | 5 | 40 | 15 |
| 5 | EC | 10 | 30 | 10 |
| 6 | EC | 20 | 2.5 | 0 |
| 7 | SC | 20 | 2.5 | 0 |
| 8 | EC | 30 | 1 | 15 |
| 9 | WG | 40 | 10 | 10 |
| 10 | WG | 50 | 5 | 5 |

Field Test 3—Lemon—Broad Mite (*Polyphagotarsonemus latus*)

Broad mite (*Polyphagotarsonemus latus*) were reared in the laboratory. The number of mites were counted, collected and then put on healthy young lemon plants. 50 mL of formulations were diluted in 100 L of water and then sprayed on the plants until ran off. After staying in a greenhouse at 21-25° C. and 80% relative atmospheric humidity for 10 days, the remaining population of mites was examined. (Table C)

TABLE C

| Test | Formulation | Methomyl (%) | Bifenthrin (%) | Mites population (%) |
|---|---|---|---|---|
| Untreated | — | 0 | 0 | 85 |
| 1 | EC | 50 | 0 | 40 |
| 2 | SC | 0 | 40 | 65 |
| 3 | EC | 5 | 20 | 15 |
| 4 | SC | 5 | 40 | 10 |
| 5 | EC | 10 | 30 | 15 |
| 6 | EC | 20 | 2.5 | 0 |
| 7 | SC | 20 | 2.5 | 5 |
| 8 | EC | 30 | 1 | 10 |
| 9 | WG | 40 | 10 | 10 |
| 10 | WG | 50 | 5 | 0 |

Field Test 4—Cotton—Burrowing Bug (*Scaptocoris castanea*)

Burrowing bug (*Scaptocoris castanea*) were reared in the laboratory. The number of aphids were counted, collected and then put on healthy young cotton plants. Formulations were diluted with water and then sprayed on the plants. After staying in a greenhouse at 21-25° C. and 80% relative atmospheric humidity for 10 days, the remaining population of bug was examined. (Table D)

TABLE D

| Test | Formulation | Methomyl (g/ha) | Bifenthrin (g/ha) | Bug population (%) |
|---|---|---|---|---|
| Untreated | — | 0 | 0 | 90 |
| 1 | EC | 600 | 0 | 50 |
| 2 | SC | 0 | 480 | 55 |
| 3 | EC | 60 | 240 | 20 |
| 4 | SC | 60 | 480 | 15 |
| 5 | EC | 120 | 360 | 10 |
| 6 | EC | 240 | 30 | 0 |
| 7 | SC | 240 | 30 | 5 |
| 8 | EC | 360 | 12 | 10 |
| 9 | WG | 480 | 120 | 5 |
| 10 | WG | 600 | 60 | 5 |

Field Test 5—Cotton—Two Spotted Spidermite (*Tetranychus urticae* Koch)

Two spotted spidermite (*Tetranychus urticae* Koch) was reared in the laboratory. The number of mite were counted, collected and then put on healthy young cotton plants. The Formulations Examples were diluted with water and then sprayed on the plants. After staying in a greenhouse at 21-25° C. and 80% relative atmospheric humidity for 10 days, the remaining population of mite was examined. (Table E)

TABLE E

| Test | Formulation | Methomyl (g/ha) | Bifenthrin (g/ha) | Spidermite population (%) |
|---|---|---|---|---|
| Untreated | — | 0 | 0 | 90 |
| 1 | EC | 600 | 0 | 40 |
| 2 | SC | 0 | 480 | 60 |
| 3 | EC | 60 | 240 | 15 |
| 4 | SC | 60 | 480 | 10 |
| 5 | EC | 120 | 360 | 10 |
| 6 | EC | 240 | 30 | 0 |
| 7 | SC | 240 | 30 | 0 |
| 8 | EC | 360 | 12 | 15 |

TABLE E-continued

| Test | Formulation | Methomyl (g/ha) | Bifenthrin (g/ha) | Spidermite population (%) |
|---|---|---|---|---|
| 9 | WG | 480 | 120 | 10 |
| 10 | WG | 600 | 60 | 0 |

Field Test 6—Cotton—Red Spidermite (*Panonychus ulmi*)

Red spidermite (*Panonychus ulmi*) was reared in the laboratory. The number of mite were counted, collected and then put on healthy young cotton plants. Formulations were diluted with water and then sprayed on the plants. After staying in a greenhouse at 21-25° C. and 80% relative atmospheric humidity for 10 days, the remaining population of mite was examined. (Table F)

TABLE F

| Test | Formulation | Methomyl (g/ha) | Bifenthrin (g/ha) | Spidermite population (%) |
|---|---|---|---|---|
| Untreated | — | 0 | 0 | 80 |
| 1 | EC | 600 | 0 | 35 |
| 2 | SC | 0 | 480 | 60 |
| 3 | EC | 60 | 240 | 15 |
| 4 | SC | 60 | 480 | 15 |
| 5 | EC | 120 | 360 | 15 |
| 6 | EC | 240 | 30 | 0 |
| 7 | SC | 240 | 30 | 5 |
| 8 | EC | 360 | 12 | 15 |
| 9 | WG | 480 | 120 | 10 |
| 10 | WG | 600 | 60 | 5 |

Field Test 7—Cotton—Broad Mite (*Polyphagotarsonemus latus*)

Broad mite (*Polyphagotarsonemus latus*) was reared in the laboratory. The number of mite were counted, collected and then put on healthy young cotton plants. Formulations Examples were diluted with water and then sprayed on the plants. After staying in a greenhouse at 21-25° C. and 80% relative atmospheric humidity for 10 days, the remaining population of mite was examined. (Table G)

TABLE G

| Test | Formulation | Methomyl (g/ha) | Bifenthrin (g/ha) | Mite population (%) |
|---|---|---|---|---|
| Untreated | — | 0 | 0 | 90 |
| 1 | EC | 600 | 0 | 40 |
| 2 | SC | 0 | 480 | 60 |
| 3 | EC | 60 | 240 | 15 |
| 4 | SC | 60 | 480 | 10 |
| 5 | EC | 120 | 360 | 15 |
| 6 | EC | 240 | 30 | 0 |
| 7 | SC | 240 | 30 | 0 |
| 8 | EC | 360 | 12 | 10 |
| 9 | WG | 480 | 120 | 5 |
| 10 | WG | 600 | 60 | 0 |

Field Test 8—Cotton—Budworm (*Heliothis virescens*)

Budworm (*Heliothis virescens*) was reared in the laboratory. The number of worm were counted, collected and then put on healthy young cotton plants. Formulations Examples were diluted with water and then sprayed on the plants. After staying in a greenhouse at 21-25° C. and 80% relative atmospheric humidity for 10 days, the remaining population of worm was examined. (Table H)

TABLE H

| Test | Formulation | Methomyl (g/ha) | Bifenthrin (g/ha) | Worm population (%) |
|---|---|---|---|---|
| Untreated | — | 0 | 0 | 90 |
| 1 | EC | 600 | 0 | 45 |
| 2 | SC | 0 | 480 | 45 |
| 3 | EC | 60 | 240 | 10 |
| 4 | SC | 60 | 480 | 10 |
| 5 | EC | 120 | 360 | 10 |
| 6 | EC | 240 | 30 | 0 |
| 7 | SC | 240 | 30 | 5 |
| 8 | EC | 360 | 12 | 10 |
| 9 | WG | 480 | 120 | 5 |
| 10 | WG | 600 | 60 | 0 |

Field Test 9—Soybean—Stink Bug (*Euschistus heros*)

Stink bugs (*Euschistus heros*) were reared in the laboratory. The number of insect were counted, collected and then put on healthy young soybean plants. The Formulations Examples were diluted and then sprayed on the plants. After staying in a greenhouse at 21-25° C. and 80% relative atmospheric humidity for 10 days, the remaining population was examined. (Table I)

TABLE I

| Test | Formulation | Methomyl (g/ha) | Bifenthrin (g/ha) | Stink bug population (%) |
|---|---|---|---|---|
| Untreated | — | 0 | 0 | 85 |
| 1 | EC | 500 | 0 | 55 |
| 2 | SC | 0 | 400 | 45 |
| 3 | EC | 50 | 200 | 10 |
| 4 | SC | 50 | 400 | 10 |
| 5 | EC | 100 | 300 | 10 |
| 6 | EC | 200 | 25 | 0 |
| 7 | SC | 200 | 25 | 0 |
| 8 | EC | 300 | 10 | 15 |
| 9 | WG | 400 | 100 | 5 |
| 10 | WG | 500 | 50 | 5 |

Field Test 10—Soybean—Stink Bug (*Piezodorus guildinii*)

Stink bug (*Piezodorus guildinii*) was reared in the laboratory. The number of insect were counted, collected and then put on healthy young soybean plants. The Formulations Examples were diluted and then sprayed on the plants. After staying in a greenhouse at 21-25° C. and 80% relative atmospheric humidity for 10 days, the remaining population was examined. (Table J)

TABLE J

| Test | Formulation | Methomyl (g/ha) | Bifenthrin (g/ha) | Stink bug population (%) |
|---|---|---|---|---|
| Untreated | — | 0 | 0 | 90 |
| 1 | EC | 500 | 0 | 50 |
| 2 | SC | 0 | 400 | 45 |
| 3 | EC | 50 | 200 | 15 |
| 4 | SC | 50 | 400 | 15 |
| 5 | EC | 100 | 300 | 10 |
| 6 | EC | 200 | 25 | 0 |
| 7 | SC | 200 | 25 | 5 |
| 8 | EC | 300 | 10 | 15 |
| 9 | WG | 400 | 100 | 5 |
| 10 | WG | 500 | 50 | 5 |

Field Test 11—Soybean—Stink Bug (*Nezara viridula*)

Stink bug (*Nezara viridula*) was reared in the laboratory. The number of insect were counted, collected and then put on healthy young soybean plants. Formulations were diluted and then sprayed on the plants. After staying in a greenhouse at 21-25° C. and 80% relative atmospheric humidity for 10 days, the remaining population was examined. (Table K)

TABLE K

| Test | Formulation | Methomyl (g/ha) | Bifenthrin (g/ha) | Stink bug population (%) |
|---|---|---|---|---|
| Untreated | — | 0 | 0 | 80 |
| 1 | EC | 600 | 0 | 40 |
| 2 | SC | 0 | 480 | 45 |
| 3 | EC | 60 | 240 | 15 |
| 4 | SC | 60 | 480 | 15 |
| 5 | EC | 120 | 360 | 10 |
| 6 | EC | 240 | 30 | 0 |
| 7 | SC | 240 | 30 | 0 |
| 8 | EC | 360 | 12 | 15 |
| 9 | WG | 480 | 120 | 10 |
| 10 | WG | 600 | 60 | 5 |

Field Test 12—Soybean—Stink Bug (*Dichelops melacanthus*)

Stink bug (*Dichelops melacanthus*) was reared in the laboratory. The number of insect were counted, collected and then put on healthy young soybean plants. Formulations were diluted and then sprayed on the plants. After staying in a greenhouse at 21-25° C. and 80% relative atmospheric humidity for 10 days, the remaining population was examined. (Table L)

TABLE L

| Test | Formulation | Methomyl (g/ha) | Bifenthrin (g/ha) | Stink bug population (%) |
|---|---|---|---|---|
| Untreated | — | 0 | 0 | 95 |
| 1 | EC | 600 | 0 | 50 |
| 2 | SC | 0 | 480 | 55 |
| 3 | EC | 60 | 240 | 10 |
| 4 | SC | 60 | 480 | 10 |
| 5 | EC | 120 | 360 | 10 |
| 6 | EC | 240 | 30 | 5 |
| 7 | SC | 240 | 30 | 5 |
| 8 | EC | 360 | 12 | 10 |
| 9 | WG | 480 | 120 | 5 |
| 10 | WG | 600 | 60 | 5 |

Field Test 13—Soybean—Soybean Looper (*Chrysodeixis Includens*)

Soybean looper (*Chrysodeixis includens*) was reared in the laboratory. The number of insect were counted, collected and then put on healthy young soybean plants. Formulations were diluted and then sprayed on the plants. After staying in a greenhouse at 21-25° C. and 80% relative atmospheric humidity for 10 days, the remaining population was examined. (Table M)

TABLE M

| Test | Formulation | Methomyl (g/ha) | Bifenthrin (g/ha) | Looper population (%) |
|---|---|---|---|---|
| Untreated | — | 0 | 0 | 90 |
| 1 | EC | 600 | 0 | 55 |
| 2 | SC | 0 | 480 | 50 |
| 3 | EC | 60 | 240 | 15 |
| 4 | SC | 60 | 480 | 10 |
| 5 | EC | 120 | 360 | 10 |
| 6 | EC | 240 | 30 | 5 |
| 7 | SC | 240 | 30 | 0 |
| 8 | EC | 360 | 12 | 15 |
| 9 | WG | 480 | 120 | 5 |
| 10 | WG | 600 | 60 | 5 |

Field Test 14—Soybean—Fall Armyworm (*Spodoptera frugiperda*)

Fall armyworm (*Spodoptera frugiperda*) was reared in the laboratory. The number of insect were counted, collected and then put on healthy young soybean plants. Formulations were diluted and then sprayed on the plants. After staying in a greenhouse at 21-25° C. and 80% relative atmospheric humidity for 10 days, the remaining population was examined. (Table N)

TABLE N

| Test | Formulation | Methomyl (g/ha) | Bifenthrin (g/ha) | Fall armyworm population (%) |
|---|---|---|---|---|
| Untreated | — | 0 | 0 | 85 |
| 1 | EC | 600 | 0 | 50 |
| 2 | SC | 0 | 480 | 50 |
| 3 | EC | 60 | 240 | 10 |
| 4 | SC | 60 | 480 | 15 |
| 5 | EC | 120 | 360 | 10 |
| 6 | EC | 240 | 30 | 0 |
| 7 | SC | 240 | 30 | 0 |
| 8 | EC | 360 | 12 | 15 |
| 9 | WG | 480 | 120 | 5 |
| 10 | WG | 600 | 60 | 5 |

Field Test 15—Soybean—Bollworm (*Helicoverpa armigera*)

Bollworm (*Helicoverpa armigera*) was reared in the laboratory. The number of insect were counted, collected and then put on healthy young soybean plants. Formulations were diluted and then sprayed on the plants. After staying in a greenhouse at 21-25° C. and 80% relative atmospheric humidity for 10 days, the remaining population was examined. (Table O)

TABLE O

| Test | Formulation | Methomyl (g/ha) | Bifenthrin (g/ha) | Bollworm population (%) |
|---|---|---|---|---|
| Untreated | — | 0 | 0 | 85 |
| 1 | EC | 700 | 0 | 45 |
| 2 | SC | 0 | 560 | 50 |
| 3 | EC | 70 | 280 | 15 |
| 4 | SC | 70 | 560 | 15 |
| 5 | EC | 140 | 420 | 10 |
| 6 | EC | 280 | 35 | 0 |
| 7 | SC | 280 | 35 | 0 |
| 8 | EC | 420 | 14 | 15 |
| 9 | WG | 560 | 140 | 5 |
| 10 | WG | 700 | 70 | 0 |

Field Test 16—Soybean—Spider Mite (*Mononychellus Planki*)

Spider mite (*Mononychellus planki*) was reared in the laboratory. The number of insect were counted, collected and then put on healthy young soybean plants. Formulations were diluted and then sprayed on the plants. After staying in a greenhouse at 21-25° C. and 80% relative atmospheric humidity for 10 days, the remaining population was examined. (Table P)

TABLE P

| Test | Formulation | Methomyl (g/ha) | Bifenthrin (g/ha) | Spider mite population (%) |
|---|---|---|---|---|
| Untreated | — | 0 | 0 | 85 |
| 1 | EC | 700 | 0 | 40 |
| 2 | SC | 0 | 560 | 65 |
| 3 | EC | 70 | 280 | 10 |
| 4 | SC | 70 | 560 | 15 |
| 5 | EC | 140 | 420 | 10 |
| 6 | EC | 280 | 35 | 0 |
| 7 | SC | 280 | 35 | 5 |
| 8 | EC | 420 | 14 | 10 |
| 9 | WG | 560 | 140 | 10 |
| 10 | WG | 700 | 70 | 5 |

Field Test 17—Soybean—Spider Mite (*Tetranychus urticae*)

Spider mite (*Tetranychus urticae*) was reared in the laboratory. The number of insect were counted, collected and then put on healthy young soybean plants. Formulations were diluted and then sprayed on the plants. After staying in a greenhouse at 21-25° C. and 80% relative atmospheric humidity for 10 days, the remaining population was examined. (Table Q)

TABLE Q

| Test | Formulation | Methomyl (g/ha) | Bifenthrin (g/ha) | Spider mite population (%) |
|---|---|---|---|---|
| Untreated | — | 0 | 0 | 90 |
| 1 | EC | 700 | 0 | 45 |
| 2 | SC | 0 | 560 | 60 |
| 3 | EC | 70 | 280 | 10 |
| 4 | SC | 70 | 560 | 15 |
| 5 | EC | 140 | 420 | 10 |
| 6 | EC | 280 | 35 | 0 |
| 7 | SC | 280 | 35 | 0 |
| 8 | EC | 420 | 14 | 10 |
| 9 | WG | 560 | 140 | 5 |
| 10 | WG | 700 | 70 | 0 |

Field Test 18—Dry Bean—Bollworm (*Helicoverpa armigera*)

Bollworm (*Helicoverpa armigera*) was reared in the laboratory. The number of insect were counted, collected and then put on healthy young dry bean plants. Formulations were diluted and then sprayed on the plants. After staying in a greenhouse at 21-25° C. and 80% relative atmospheric humidity for 10 days, the remaining population was examined. (Table R)

TABLE R

| Test | Formulation | Methomyl (g/ha) | Bifenthrin (g/ha) | Bollworm population (%) |
|---|---|---|---|---|
| Untreated | — | 0 | 0 | 95 |
| 1 | EC | 600 | 0 | 50 |
| 2 | SC | 0 | 480 | 50 |
| 3 | EC | 60 | 240 | 10 |
| 4 | SC | 60 | 480 | 15 |
| 5 | EC | 120 | 360 | 10 |
| 6 | EC | 240 | 30 | 0 |
| 7 | SC | 240 | 30 | 0 |
| 8 | EC | 360 | 12 | 15 |
| 9 | WG | 480 | 120 | 5 |
| 10 | WG | 600 | 60 | 0 |

Field Test 19—Tomato—Fruit Borer (*Neoleucinodes Elegantalis*)

Larva of fruit borer (*Neoleucinodes elegantalis*) was reared in the laboratory. The number of insect were counted, collected and then put on healthy young tomato plants. 50 mL of formulations were diluted with 100 L of water and then sprayed on the plants until ran off. After staying in a greenhouse at 21-25° C. and 80% relative atmospheric humidity for 10 days, the remaining population of borer was examined. (Table S)

TABLE S

| Test | Formulation | Methomyl (%) | Bifenthrin (%) | Borer population (%) |
|---|---|---|---|---|
| Untreated | — | 0 | 0 | 90 |
| 1 | EC | 50 | 0 | 45 |
| 2 | SC | 0 | 40 | 50 |
| 3 | EC | 5 | 20 | 10 |
| 4 | SC | 5 | 40 | 15 |
| 5 | EC | 10 | 30 | 10 |
| 6 | EC | 20 | 2.5 | 5 |
| 7 | SC | 20 | 2.5 | 5 |
| 8 | EC | 30 | 1 | 15 |
| 9 | WG | 40 | 10 | 5 |
| 10 | WG | 50 | 5 | 5 |

Field Test 20—Potato—Potato Tuber Moth (*Phthorimaea operculella*)

Larva of moths (*Phthorimaea operculella*) were reared in the laboratory. The number of larvae were counted, collected and then put on healthy young potato plants. 50 mL of the formulations were diluted in 100 L of water and then sprayed on the plants until ran off. After staying in a greenhouse at 21-25° C. and 80% relative atmospheric humidity for 10 days, the remaining population of larvae was examined. (Table T)

TABLE T

| Test | Formulation | Methomyl (%) | Bifenthrin (%) | Larva population (%) |
|---|---|---|---|---|
| Untreated | — | 0 | 0 | 90 |
| 1 | EC | 50 | 0 | 45 |
| 2 | SC | 0 | 40 | 45 |
| 3 | EC | 5 | 20 | 10 |
| 4 | SC | 5 | 40 | 10 |
| 5 | EC | 10 | 30 | 10 |
| 6 | EC | 20 | 2.5 | 0 |
| 7 | SC | 20 | 2.5 | 0 |
| 8 | EC | 30 | 1 | 15 |
| 9 | WG | 40 | 10 | 5 |
| 10 | WG | 50 | 5 | 5 |

Field Test 21—Melon—Melonworm Moth (*Diaphania Hyalinata*)

Larva of moths (*Diaphania hyalinata*) were reared in the laboratory. The number of larvae were counted, collected and then put on healthy young potato plants. 100 mL of the formulations were diluted in 100 L of water and then sprayed on the plants until ran off. After staying in a greenhouse at 21-25° C. and 80% relative atmospheric humidity for 10 days, the remaining population of larvae was examined. (Table U)

TABLE U

| Test | Formulation | Methomyl (%) | Bifenthrin (%) | Larva population (%) |
|---|---|---|---|---|
| Untreated | — | 0 | 0 | 95 |
| 1 | EC | 50 | 0 | 45 |
| 2 | SC | 0 | 40 | 55 |
| 3 | EC | 5 | 20 | 10 |
| 4 | SC | 5 | 40 | 15 |
| 5 | EC | 10 | 30 | 10 |
| 6 | EC | 20 | 2.5 | 0 |
| 7 | SC | 20 | 2.5 | 0 |
| 8 | EC | 30 | 1 | 15 |
| 9 | WG | 40 | 10 | 5 |
| 10 | WG | 50 | 5 | 0 |

Field Test 22—Melon—Pickleworm (*Diaphania nitidalis*)

Larva of moths (*Diaphania nitidalis*) were reared in the laboratory. The number of larvae were counted, collected and then put on healthy young potato plants. 100 mL of the formulations were diluted in 100 L of water and then sprayed on the plants until ran off. After staying in a greenhouse at 21-25° C. and 80% relative atmospheric humidity for 10 days, the remaining population of larvae was examined. (Table V)

TABLE V

| Test | Formulation | Methomyl (%) | Bifenthrin (%) | Larva population (%) |
|---|---|---|---|---|
| Untreated | — | 0 | 0 | 90 |
| 1 | EC | 50 | 0 | 50 |
| 2 | SC | 0 | 40 | 55 |
| 3 | EC | 5 | 20 | 10 |
| 4 | SC | 5 | 40 | 10 |
| 5 | EC | 10 | 30 | 10 |
| 6 | EC | 20 | 2.5 | 0 |
| 7 | SC | 20 | 2.5 | 0 |
| 8 | EC | 30 | 1 | 10 |
| 9 | WG | 40 | 10 | 5 |
| 10 | WG | 50 | 5 | 0 |

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The invention claimed is:

1. An insecticidal composition comprising:
    at least one carbamate insecticide, the at least one carbamate insecticide including methomyl in an amount of from 5-50% by weight of the composition; and
    at least one pyrethroid insecticide, the at least one pyrethroid insecticide including bifenthrin in an amount of from 1-40% by weight of the composition.
2. The composition according to claim 1, wherein the at least one carbamate insecticide further includes methiocarb, oxamyl, pirimicarb and/or thiodicarb.
3. The composition according to claim 1, wherein the at least one carbamate insecticide consists of methomyl.
4. The composition according to claim 1, wherein the at least one pyrethroid insecticide further includes cypermethrin, esfenvalerate, etofenprox and/or tefluthrin.
5. The composition according to claim 1, wherein the at least one pyrethroid insecticide consists of bifenthrin.
6. The composition according to claim 1, wherein the weight ratio of the at least one carbamate insecticide to the at least one pyrethroid insecticide is from 99:1 to 1:99.
7. The composition according to claim 6, wherein the weight ratio is from 1:12 to 12:1.
8. The composition according to claim 1 further comprising one or more auxiliaries selected from extenders, carriers, solvents, surfactants, stabilizers, anti-foaming agents, anti-freezing agents, preservatives, antioxidants, colorants, thickeners, solid adherents and inert fillers.
9. A method for preventing, controlling and/or treating insect infestations in plants, plant parts and/or their surroundings, comprising, applying to the plants, plant parts and/or their surroundings a composition including at least one carbamate insecticide, the at least one carbamate insecticide including methomyl in an amount of from 5-50% by weight of the composition, and the composition including at least one pyrethroid insecticide, the at least one pyrethroid insecticide including bifenthrin in an amount of from 1-40% by weight of the composition.
10. The method according to claim 9, wherein the plants, plant parts or their surroundings are selected from cereals, citrus, cucurbitaceae, fibre plants, fruits, leguminous plants, ornamentals and vegetables, corn, cotton, dry bean, lemon, melon, orange, papaya, potato, rose, soybean, tomato and wheat.
11. The method according to claim 9, wherein the insects are selected from aphids, armyworms, beetles, bollworm, budworms, pickleworm, burrowing bugs, borers, caterpillars, citrus *Orthezia*, Great Southern White, leafhoppers, leafminers, loopers, millipedes, broad mites, moths, spider mites, stink bugs, thrips, weevils, whiteflies, worms, and psylla.
12. A method for controlling and/or treating insect infestations in plants, plant parts and/or their surroundings, comprising, applying to the plants, plant parts and/or their surroundings a composition including at least one carbamate insecticide, the at least one carbamate insecticide including methomyl in an amount of from 5-50% by weight of the composition, and the composition including at least one pyrethroid insecticide, the at least one pyrethroid insecticide including bifenthrin in an amount of from 1-40% by weight of the composition.

* * * * *